United States Patent
Yonce et al.

(10) Patent No.: US 7,286,876 B2
(45) Date of Patent: Oct. 23, 2007

(54) TEMPLATE-BASED CAPTURE VERIFICATION FOR MULTI-SITE PACING

(75) Inventors: David J. Yonce, Fridley, MN (US); David Ternes, Roseville, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 730 days.

(21) Appl. No.: 10/251,629

(22) Filed: Sep. 19, 2002

(65) Prior Publication Data

US 2003/0083711 A1    May 1, 2003

Related U.S. Application Data

(63) Continuation-in-part of application No. 10/003,718, filed on Oct. 26, 2001, now Pat. No. 7,177,689.

(51) Int. Cl.
*A61N 1/368* (2006.01)
(52) U.S. Cl. .................................................. 607/28
(58) Field of Classification Search ............. 600/372, 600/373, 374, 377, 393, 509; 607/4, 5, 9, 607/28, 116, 119, 122, 123
See application file for complete search history.

(56) References Cited

U.S. PATENT DOCUMENTS

| | | | |
|---|---|---|---|
| 4,832,041 A | 5/1989 | Wang et al. ............... 128/697 |
| 4,895,152 A | 1/1990 | Callaghan et al. | |
| 5,273,049 A | 12/1993 | Steinhaus et al. ........... 128/696 |
| 5,312,445 A | 5/1994 | Nappholz et al. ............. 607/9 |
| 5,330,511 A | 7/1994 | Boute | |
| 5,331,966 A | 7/1994 | Bennett et al. ............. 128/696 |
| 5,334,220 A | 8/1994 | Sholder | |
| 5,340,361 A | 8/1994 | Sholder | |
| 5,350,410 A | 9/1994 | Kleks et al. | |
| 5,391,192 A | 2/1995 | Lu et al. ...................... 607/28 |
| 5,458,623 A | 10/1995 | Lu et al. | |
| 5,534,016 A * | 7/1996 | Boute ........................... 607/9 |
| 5,626,623 A | 5/1997 | Kieval et al. | |
| 5,660,184 A | 8/1997 | Donehoo et al. ........... 128/696 |
| 5,674,254 A | 10/1997 | van Krieken ................ 607/11 |
| 5,741,308 A | 4/1998 | Sholder | |
| 5,755,739 A | 5/1998 | Sun et al. ..................... 607/14 |
| 5,771,898 A | 6/1998 | Marinello ................... 128/697 |
| 5,778,881 A | 7/1998 | Sun et al. ................... 128/696 |
| 5,782,888 A | 7/1998 | Sun et al. ..................... 607/27 |
| 6,029,088 A * | 2/2000 | Budgifvars et al. ........... 607/27 |

(Continued)

FOREIGN PATENT DOCUMENTS

EP    1123716    8/2001

(Continued)

*Primary Examiner*—Robert E. Pezzuto
*Assistant Examiner*—Frances P. Oropeza
(74) *Attorney, Agent, or Firm*—Schwegman, Lundberg, Woessner, & Kluth, P.A.

(57) ABSTRACT

An apparatus and method for verifying capture by first and second pacing pulses in which an evoked response waveform recorded during a pacing event is compared with template waveforms representing capture by the first, second, and both pacing pulses. The evoked response is then classified as representing a type of capture represented by a template waveform if the evoked response waveform highly correlates with one template waveform and has correlation values with the other template waveforms within specified bounds.

20 Claims, 9 Drawing Sheets

U.S. PATENT DOCUMENTS

| | | | |
|---|---|---|---|
| 6,101,416 A | 8/2000 | Sloman | 607/28 |
| 6,128,535 A | 10/2000 | Maarse | |
| 6,169,921 B1 | 1/2001 | KenKnight et al. | 607/4 |
| 6,253,102 B1 | 6/2001 | Hsu et al. | |
| 6,304,773 B1* | 10/2001 | Taylor et al. | 600/515 |
| 6,456,881 B1 | 9/2002 | Bornzin | |
| 6,512,953 B2* | 1/2003 | Florio et al. | 607/28 |
| 6,609,023 B1 | 8/2003 | Fischell et al. | |
| 6,697,673 B1* | 2/2004 | Lu | 607/28 |
| 6,738,669 B1 | 5/2004 | Sloman et al. | |
| 6,829,505 B2 | 12/2004 | Kramer et al. | |
| 2001/0049542 A1 | 12/2001 | Florio et al. | 607/28 |
| 2001/0049543 A1 | 12/2001 | Kroll | |
| 2002/0193696 A1 | 12/2002 | Hsu et al. | |
| 2003/0083710 A1 | 5/2003 | Ternes et al. | 607/27 |
| 2003/0083711 A1 | 5/2003 | Yonce et al. | 607/27 |
| 2004/0158165 A1 | 8/2004 | Yonce et al. | |
| 2004/0158293 A1 | 8/2004 | Yonce et al. | |

FOREIGN PATENT DOCUMENTS

| | | |
|---|---|---|
| EP | 1155711 | 11/2001 |
| WO | WO-03/020366 A1 | 3/2003 |
| WO | WO-03/037428 A2 | 5/2003 |
| WO | WO-2004/026398 A1 | 4/2004 |
| WO | WO-2005053792 A1 | 6/2005 |

* cited by examiner

TEMPLATE-BASED CAPTURE VERIFICATION FOR MULTI-SITE PACING

CROSS-REFERENCE TO RELATED APPLICATION(S)

This application is a continuation-in-part of U.S. application Ser. No. 10/003,718, filed on Oct. 26, 2001 now U.S. Pat. No. 7,177,689, the specification of which is incorporated by reference herein.

FIELD OF THE INVENTION

This invention pertains to cardiac pacemakers and, in particular, to systems and methods for ascertaining the performance of the device and adjusting pacing parameters accordingly.

BACKGROUND

Implantable cardiac pacemakers are a class of cardiac rhythm management devices that provide electrical stimulation in the form of pacing pulses to selected chambers of the heart. (As the term is used herein, a pacemaker is any cardiac rhythm management device with a pacing functionality regardless of any additional functions it may perform such as cardioversion/defibrillation.) Pacemakers typically have a programmable electronic controller that causes the pacing pulses to be output in response to lapsed time intervals and sensed electrical activity (i.e., intrinsic heart beats). Most pacemakers are programmed to operate in a so-called demand mode (a.k.a., synchronous mode), where a pacing pulse is delivered to a heart chamber during a cardiac cycle only when no intrinsic beat by the chamber is detected. An escape interval is defined for each paced chamber, which is the minimum time interval in which a beat must be detected before a pace will be delivered. The ventricular escape interval thus defines the minimum rate at which the pacemaker will allow the heart to beat, sometimes referred to as the lower rate limit. If functioning properly, the pacemaker in this manner makes up for a heart's inability to pace itself at an appropriate rhythm.

In order for a pacemaker to control the heart rate in the manner described above, the paces delivered by the device must achieve "capture," which refers to causing sufficient depolarization of the myocardium that a propagating wave of excitation and contraction result (i.e., a heart beat). A pacing pulse that does not capture the heart is thus an ineffective pulse. This not only wastes energy from the limited energy resources (battery) of pacemaker, but can have deleterious physiological effects as well, since a demand pacemaker that is not achieving capture is not performing its function in enforcing a minimum heart rate. A number of factors can determine whether a given pacing pulse will achieve capture, but the principal factor of concern here is the energy of the pulse, which is a function of the pulse's amplitude and duration. The minimum pacing pulse energy necessary to achieve capture by a particular pacing channel is referred to as the capture threshold. Programmable pacemakers enable the amplitude and pulse width of pacing pulses to be adjusted, along with other parameters. It is common practice to determine the capture threshold by initially pacing with a high energy to ensure capture and then progressively lowering the pacing pulse energy during a sequence of cardiac cycles until capture is no longer achieved. The pacing pulse energy can then be adjusted to an appropriate value in accordance with the determined capture threshold by setting it equal to the capture threshold plus a specified safety margin.

A common technique used to determine if capture is present during a given cardiac cycle is to look for an "evoked response" immediately following a pacing pulse. The evoked response is the wave of depolarization that results from the pacing pulse and evidences that the paced chamber has responded appropriately and contracted. By detecting an evoked atrial or ventricular depolarization that exceeds a specified value (i.e., corresponding to an evoked P-wave or evoked R-wave, respectively, on a surface electrocardiogram or their equivalents in an internal electrogram), the pacemaker is able to detect whether the pacing pulse (A-pulse or V-pulse) was effective in capturing the heart, that is, causing a contraction in the respective heart chamber. Capture verification can be performed in the clinical setting, with the clinician then adjusting pacing parameters so that the heart is reliably paced. It is desirable, however, for the pacemaker itself to be capable of verifying capture so that loss of capture can be detected when it occurs with pacing parameters then adjusted automatically, a function known as autocapture. (See, e.g., U.S. Pat. No. 6,169,921 issued to KenKnight, et. al. and presently assigned to Cardiac Pacemakers, Inc.) An autocapture function provides the pacemaker with extended longevity, greater ease of use, and greater patient safety.

Also included within the concept of cardiac rhythm is the manner and degree to which the heart chambers contract during a cardiac cycle to result in the efficient pumping of blood. For example, the heart pumps more effectively when the chambers contract in a coordinated manner. The heart has specialized conduction pathways in both the atria and the ventricles that enable the rapid conduction of excitation (i.e., depolarization) throughout the myocardium. These pathways conduct excitatory impulses in a manner that results in a coordinated contraction of both atria and both ventricles.

Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output. The resulting diminishment in cardiac output may be significant in a patient with congestive heart failure (CHF) whose cardiac output is already compromised. Intraventricular and/or interventricular conduction defects can also be a cause of CHF in some patients. In order to treat these problems, pacemakers have been developed which provide electrical pacing stimulation to one or both of the atria and/or ventricles during a cardiac cycle in an attempt to improve the coordination of atrial and/or ventricular contractions, termed cardiac resynchronization therapy. To optimize the cardiac output for some heart failure patients, for example, the right and left ventricles are paced synchronously with a determined time offset, termed biventricular pacing.

Multi-site resynchronization pacing, however, is problematic for conventional capture verification methods based upon evoked response detection as described above. In biventricular pacing, for example, the proximity in time of resynchronization paces to the left and right ventricles may prevent an evoked response caused by the first pace from being distinguished from the second pace. In addition, the second pace could interfere with evoked response sensing when the evoked response from the first pace occurs within an amplifier blanking interval initiated by the second pace.

SUMMARY OF THE INVENTION

A depolarization waveform, such as a surface electrocardiogram (ECG) or internal electrogram, recorded during a paced event that achieves capture exhibits morphological differences from that recorded during a paced event that fails to achieve capture. Also, when multiple pacing pulses are delivered to either the atria or the ventricles during a cardiac cycle, the morphology of the depolarization waveform that results is affected if even one of the pacing pulses fails to achieve capture. In accordance with the invention, capture of the heart by a pacing pulse is verified by comparing an evoked response or test depolarization waveform recorded during the paced event with a reference template waveform representing capture of the heart by a similarly delivered pacing pulse. The comparison may be done by cross-correlating the reference template and test waveforms so that loss of the capture is detected when the two waveforms become uncorrelated. In a multi-site pacing situation, template waveforms representing capture by each pace individually and by all of the paces collectively can be used to determine which pace failed to achieve capture and to simplify the determination of capture thresholds for each pacing site.

In a situation where first and second pacing pulses are output to either the atria or ventricles during a cardiac cycle, capture by both pacing pulses may be detected if a recorded evoked response waveform is highly correlated with a template waveform representing capture by both pacing pulses and, additionally, is correlated with template waveforms representing capture by only the first pacing pulse and capture by only the second pacing pulse only to a specified extent. In an exemplary embodiment, biventricular capture is detected if the evoked response highly correlates with a template waveform representing biventricular capture and correlates with templates representing right ventricular and left ventricular capture to roughly the same extent as does the biventricular capture template.

DETAILED DESCRIPTION

Figure 1:
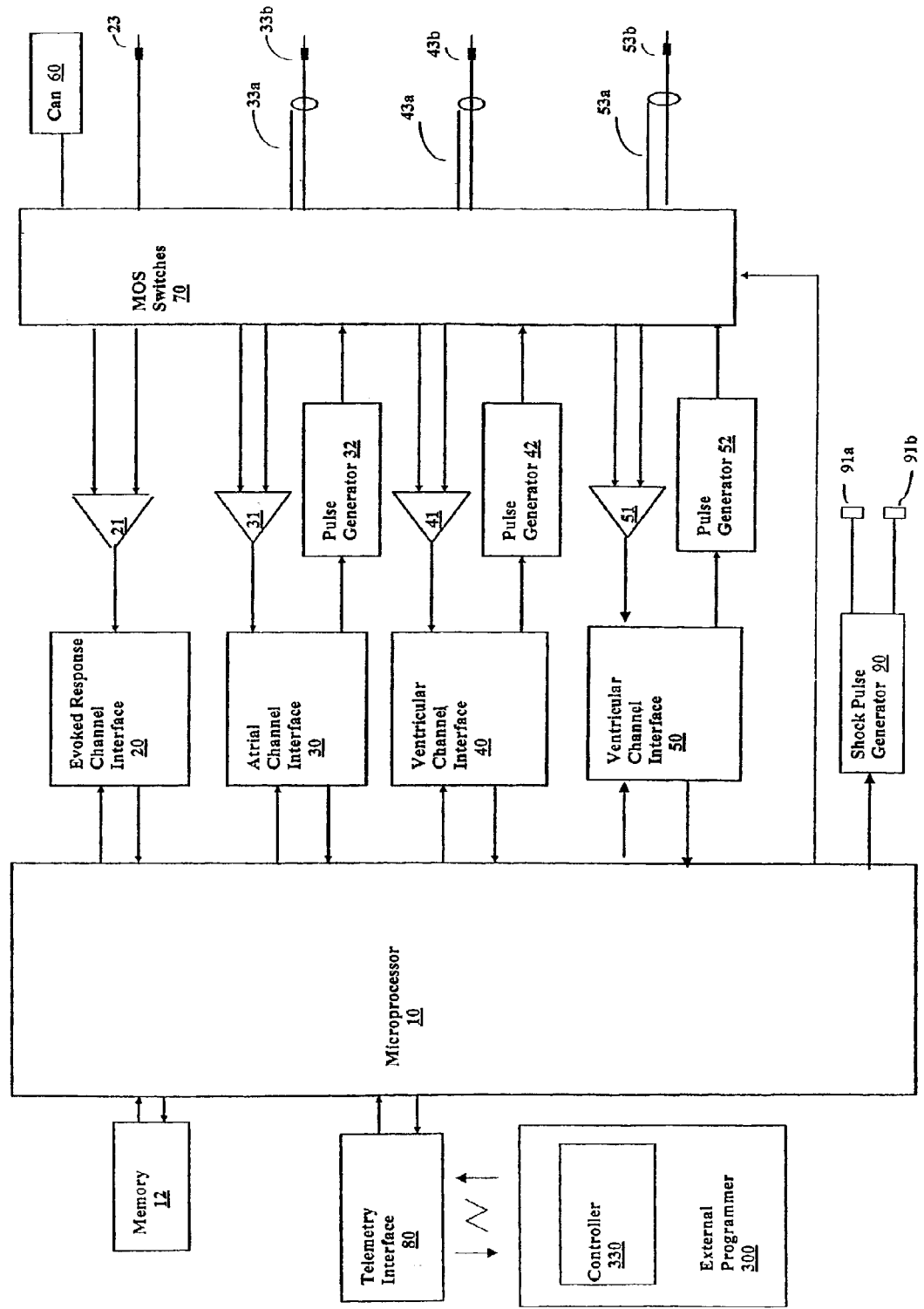
FIG. 1 is a block diagram of a multi-site pacemaker.

The present invention may be incorporated into pacemakers having a number of different pacing configurations, including multi-site pacing configurations for delivering various types of resynchronization therapy where a pace is delivered to each of the paired atria and/or ventricles during a cardiac cycle or where multiple paces are delivered to a single chamber. For illustrative purposes, however, the invention will be described with reference to a dual-chamber pacemaker (i.e., one that senses and/or paces both the atria and ventricles) having two ventricular pacing channels for pacing both ventricles or delivering two paces to a single ventricle as shown in FIG. 1.

a. Hardware Platform

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above the capture threshold must be delivered to the chamber.

The controller of the pacemaker is made up of a microprocessor 10 communicating with a memory 12, where the memory 12 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the pacemaker in a number of programmed modes where a programmed mode defines how pacing pulses are output in response to sensed events and expiration of time intervals. A telemetry interface 80 is provided for communicating with an external programmer 300. The external programmer is a computerized device with a controller 330 that can interrogate the pacemaker and receive stored data as well as adjust the operating parameters of the pacemaker.

The pacemaker has an atrial sensing/pacing channel comprising ring electrode 33*a*, tip electrode 33*b*, sense amplifier 31, pulse generator 32, and an atrial channel interface 30 which communicates bidirectionally with a port of microprocessor 10. The device also has two ventricular sensing/pacing channels that similarly include ring electrodes 43*a* and 53*a*, tip electrodes 43*b* and 53*b*, sense amplifiers 41 and 51, pulse generators 42 and 52, and ventricular channel interfaces 40 and 50. For each channel, the electrodes are connected to the pacemaker by a lead and used for both sensing and pacing. A MOS switching network 70 controlled by the microprocessor is used to switch the electrodes from the input of a sense amplifier to the output of a pulse generator. A shock channel is also provided comprising a shock pulse generator 90 and shock electrodes 91*a* and 91*b* that enables the device to deliver a defibrillation shock to the heart when fibrillation or other tachyarrhythmia is detected. The pacemaker also has an evoked response sensing channel that comprises an evoked response channel interface 20 and a sense amplifier 21 that has its differential inputs connected to a unipolar electrode 23 and to the device housing or can 60 through the switching network 70. The evoked response sensing channel may be used to verify that a pacing pulse has achieved capture of the heart in a conventional manner or, as explained below, used to record an evoked response electrogram.

The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or adjusting the pacing pulse energy by changing the pulse amplitude or pulse width. The microprocessor 10 controls the overall operation of the device in accordance with programmed instructions stored in memory. The sensing circuitry of the pacemaker generates atrial and ventricular sense signals when voltages sensed by the electrodes exceed a specified threshold. The controller then interprets sense signals from the sensing channels and controls the delivery of paces in accordance with a programmed pacing mode. The sense signals from any of the sensing channels of the pacemaker in FIG. 1 can be digitized and recorded by the controller to constitute an electrogram that can either be transmitted via the telemetry link 80 to the external programmer 300 or stored for later transmission. The patient's cardiac activity may thus be observed in real-time or over a selected historical period.

The electrical response of the heart to a pacing pulse is referred to as an evoked response. If the evoked response indicates that a propagating wave of depolarization has resulted from the pacing pulse, it evidences that the paced chamber has responded appropriately and contracted. An evoked response can therefore be used to verify that the pace has achieved capture of the heart. In accordance with the invention, an electrogram can also be recorded of an evoked response to a pace and used to determine if capture is achieved by comparing the recorded electrogram with a template electrogram representing capture of the heart by a similarly delivered pace. An evoked response sensing channel for recording an electrogram can be a sensing channel normally used for other purposes or can be a sensing channel dedicated to sensing evoked responses. It is preferable to record the electrogram with a unipolar electrode that "sees" a larger volume of the myocardium as a wave of electrical activity spreads than a bipolar electrode. In the embodiment illustrated in FIG. 1, the atrial and ventricular sensing pacing channels utilize bipolar electrodes, and a dedicated evoked response sensing channel is provided with a unipolar electrode. Alternate embodiments may employ unipolar electrodes in the atrial and/or sensing/pacing channels, in which case unipolar sensing of an evoked response may be performed with those channels instead of a dedicated channel. The evoked response sensing channel may also be implemented by the shock channel wherein the shock leads normally used for delivering defibrillation shocks to the heart are switched to a sensing amplifier by the switch matrix 70.

b. Template-based Capture Verification and Threshold Determination

In accordance with the invention, capture of heart by multiple pacing pulses delivered to the atria and/or ventricles during a cardiac cycle is verified by recording an evoked response waveform during the pacing cycle, also referred to herein as a test depolarization waveform, and comparing the recorded waveform with a template depolarization waveform representing capture of the heart by at least one pacing pulse. Although the method described herein for capture verification and threshold determination may be applied to any multi-site pacing configuration, the following detailed explanation and description of specific embodiments will be confined to a biventricular pacing configuration where both ventricles are paced during a cardiac cycle separated by a programmed offset.

Figures 2A, 2B, 3A:
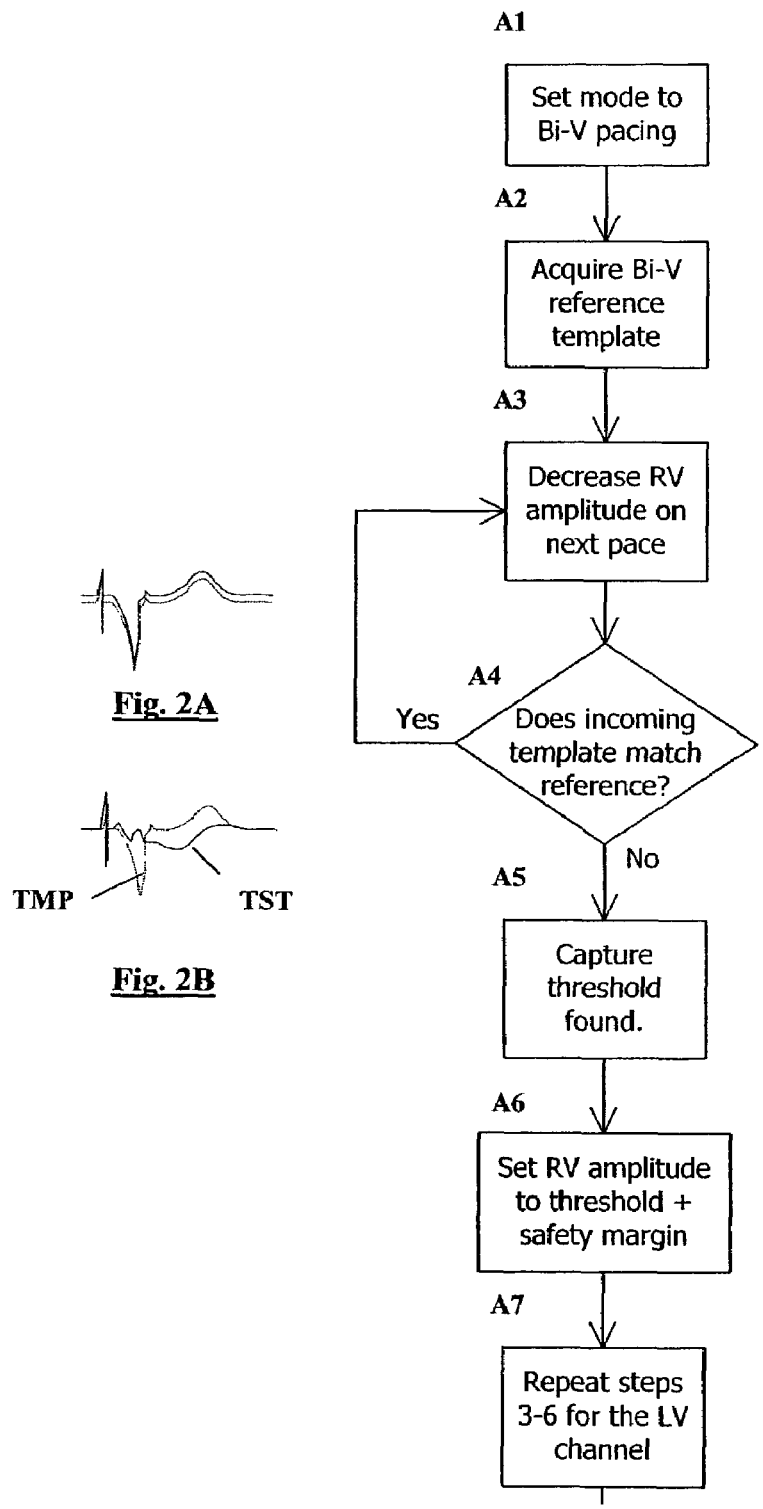
FIGS. 2A and 2B illustrate an ECG recorded after a pace and a template ECG.
FIGS. 3A and 3B illustrate exemplary embodiments of algorithms for capture threshold determination.

Delivery of multiple paces to the ventricles during a cardiac cycle changes the pattern of the resulting depolarization as compared with the pattern that results from a single ventricular pace. This difference appears as a QRS wave morphology change in a recorded depolarization waveform such as a surface ECG or electrogram that senses the time-varying net dipole vector produced by the depolarization. A reference template waveform can be created by recording a ventricular ECG or electrogram during a biventricular pacing cycle that is known to achieve capture with both pacing pulses. Presence or absence of capture for a given pace can then be determined by comparing the template waveform with a test depolarization waveform recorded during the pace. FIG. 2A shows an example of a template ECG waveform TMP and a test ECG waveform TST that match, while FIG. 2B show test and template waveforms that are morphologically different because of a failure to achieve capture by one of the pacing pulses.

In an exemplary implementation, the degree of similarity between a test waveform and a template waveform is ascertained by performing a time-domain cross-correlation between the waveforms. Loss of capture at one of the ventricular pacing sites is then indicated by a loss of correlation between the test and template waveforms. The exact correlation values that should optimally be used in deciding whether or not a test waveform and template waveform match may be selected on the basis of empiric testing as the optimum values may vary for an individual patient and/or pacemaker. Capture verification performed in this manner may be used to determine the capture threshold of a pacing channel by varying the pacing pulse energy and finding the minimum energy that results in capture.

Capture verification and threshold determination as described above may be implemented in a number of different ways. In one exemplary embodiment, a surface ECG is recorded with conventional leads during pacing by an external programmer that communicates with the implanted pacemaker via a radio telemetry link. The processor of the external programmer then performs the correlation between the test ECG and a template ECG to determine if capture is achieved by the pacing pulses. In a modification to this embodiment, rather than using surface ECGs, a test electrogram recorded by an evoked response sensing channel of the pacemaker and transmitted to the external programmer is compared with a template electrogram to verify capture. The external programmer can employ the telemetry link to adjust the pacing pulse energy in order to determine the capture threshold and then set the pacing pulse energy at an appropriate value, either under the direction of a clinician or automatically by software running in the external programmer.

In another embodiment, the controller of the pacemaker is programmed to verify capture by comparing the test electrogram with the template electrogram and to determine the capture threshold by varying the pacing pulse energy, either autonomously at selected times or in accordance with instructions received over the telemetry link. The controller may then be further programmed to automatically set the pacing pulse energy in accordance with the determined capture threshold. Determination of the capture threshold may be performed automatically on a periodic basis or at the direction of a clinician communicating with an external programmer. The controller may also be programmed to verify capture by pacing pulses on a beat-to-beat basis. If a loss of capture is detected, the controller can then perform a capture threshold determination and adjust the pacing pulse energy as appropriate. Loss of capture events may also be logged in the memory of the controller for later transmission to an external programmer.

FIG. 3A illustrates an exemplary procedure for determining the threshold voltage of the right and left ventricular pacing channels (referred to as RV and LV, respectively) in a bi-ventricular pacemaker using ECG or electrogram waveforms. The auto-threshold algorithm begins at steps A1 and A2 by pacing both chambers of the heart and recording an ECG or electrogram to create a biventricular (Bi-V) template waveform that is to be used as a reference. The pacing pulse amplitude for both ventricles is set at a relatively high value to ensure capture during acquisition of the biventricular template waveform. After the template waveform is obtained, the system decreases one of the pacing amplitudes at step A3, in this case the RV pacing amplitude, before the next pace. The RV pace triggers the recording of an incoming ECG or electrogram following the pace that is to be used as the test waveform in verifying capture. A cross correlation is performed between the template waveform and the test waveform at step A4. If the waveforms correlate well, then both ventricular pacing channels are assumed to have achieved capture and step A3 is repeated to decrease the RV pacing amplitude. If loss of correlation is detected at step A4, then the RV pacing amplitude is assumed to have dropped below the threshold voltage. The capture threshold is then determined at step A5 to be the RV pacing amplitude before the decrease at step A3. The system then sets the RV pacing pulse amplitude to the threshold voltage plus some safety factor at step A6. Steps A3 through A6 are then repeated for the LV pacing channel as indicated by step A7 in order find the LV capture threshold and set the LV pacing amplitude.

In single-site pacing systems utilizing capture verification, it is desirable to quickly pace the heart once a loss of capture occurs. This becomes especially important with pacing-dependent patients in order to maintain cardiac activity. Often the delay associated with the external programmer ECG and with the telemetry systems used for communication between the external programmer and the pacemaker can prohibit immediate safety pacing. Note, however, that the bi-ventricular auto-threshold algorithm presented above inherently includes a safety back-up pace with the additional ventricular pacing channel. Once one channel loses capture, the other still causes contraction of the ventricles, maintaining ventricular function. Because of the safety provided by two ventricular pacing sites, the auto-threshold algorithm could also start with one output high and increase the other from a sub-threshold voltage. (This is undesirable for more than a few cycles, of course, since the benefits of resynchronization therapy are lost if biventricular capture does not occur.) For example, a template can be created for RV-only pacing. The LV pacing amplitude then increases from a sub-threshold voltage until the system detects Bi-V pacing. This flexibility thus facilitates the use of more efficient search algorithms to speed convergence to the proper threshold value.

Figure 3B:
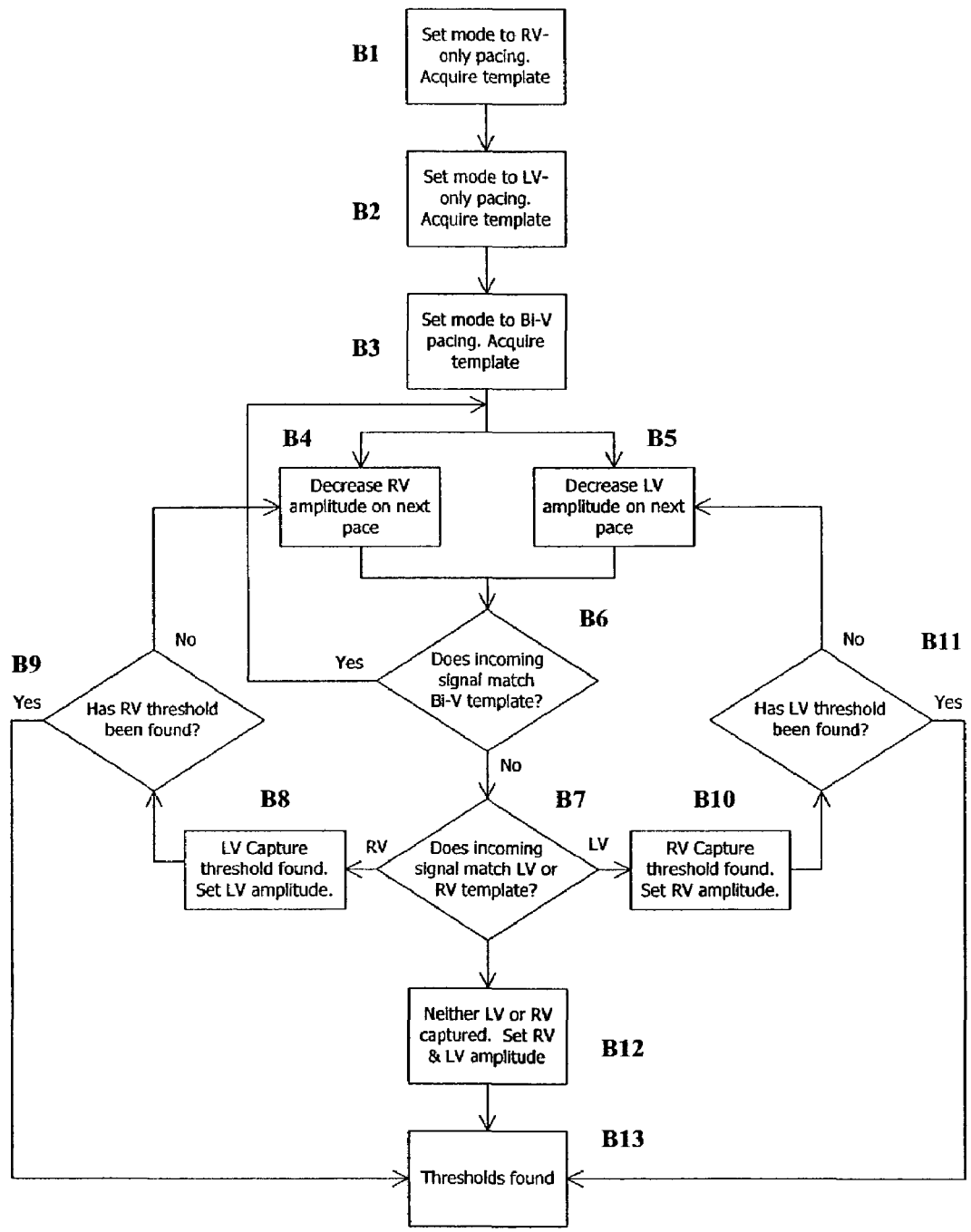

Another exemplary procedure is illustrated by FIG. 3B that decreases the total time of the auto-threshold algorithm by determining the LV and RV capture thresholds simultaneously. The algorithm first acquires templates in the RV-only, LV-only, and Bi-V pacing configurations at steps B1, B2, and B3. After creation of the templates, the system begins decreasing RV and LV pacing amplitudes simultaneously with each pace as indicated by steps B4 and B5, respectively. Similar to the previous algorithm, the RV pace triggers the creation of a test waveform. Cross correlations are then performed between the test waveform and the three templates. If a high correlation exists between the test waveform and the Bi-V template at step B6, both pace amplitudes are assumed to still be above the capture threshold value and the algorithm returns to steps B4 and B5. Otherwise cross-correlations between the test waveform and the RV-only and LV-only templates are performed at step B7. If a high correlation exists between the LV-only template and the test waveform, then the RV pacing amplitude has dropped below the threshold voltage, and the RV capture threshold is found at step B10. Likewise, a high correlation between the test waveform and the RV-only template indicates that the LV pace amplitude has dropped below the threshold voltage, and the LV capture threshold is found at step B8. If a capture threshold is found for a pacing channel at either step B8 or B10, steps B9 and B11 then test whether a capture threshold for the other pacing channel has been found so that the procedure can either end at step B13 or return to step B4 or B5. If the system indicates no correlation between the test waveform and any of the templates, then both pacing channels have dropped below the threshold value. The capture thresholds for both pacing channels are then found so that the pacing thresholds can be adjusted accordingly as indicated by steps B12 and B13.

Figure 4A:
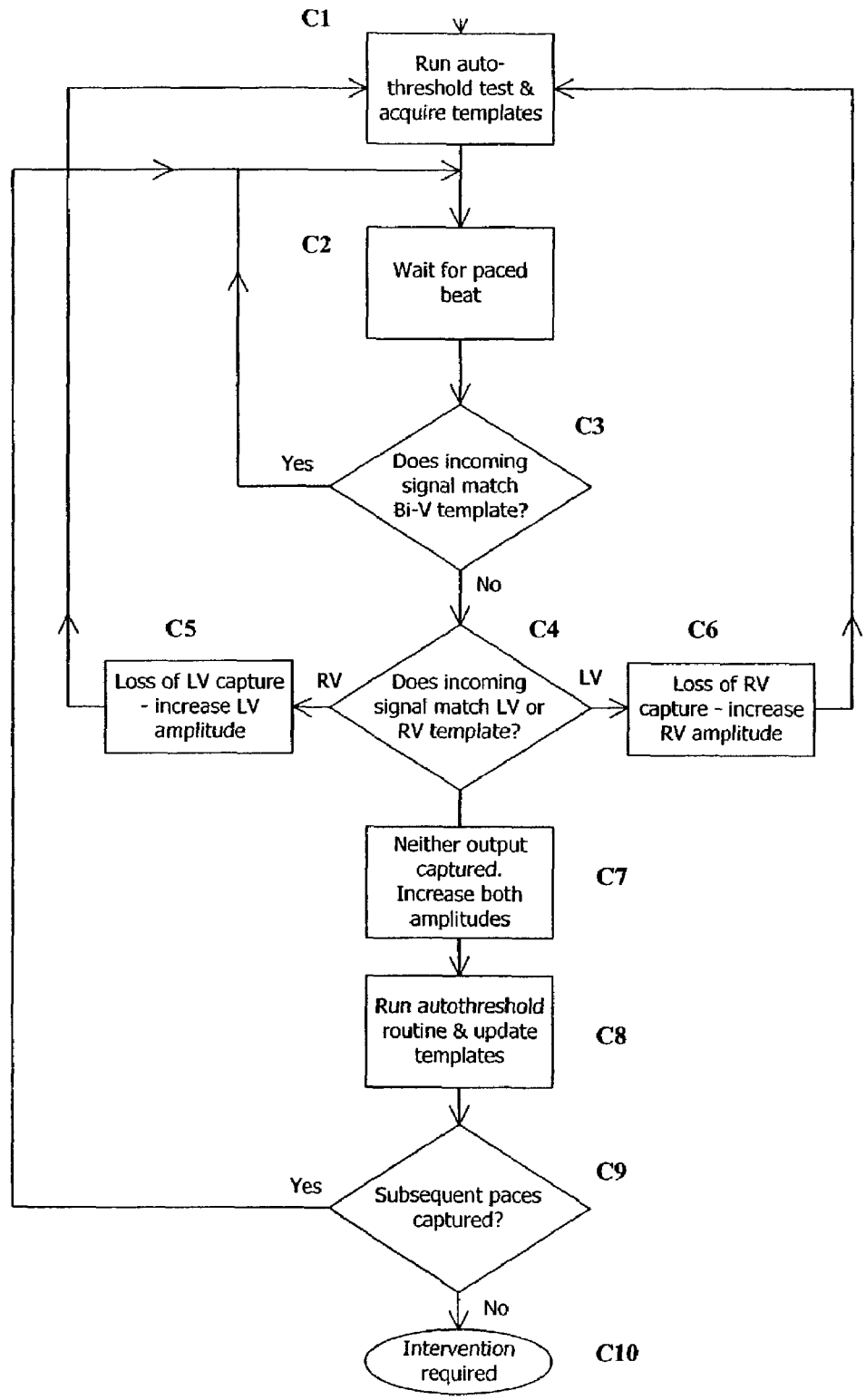
FIGS. 4A and 4B illustrate exemplary embodiments of an auto-capture algorithm.
Figure 4B:
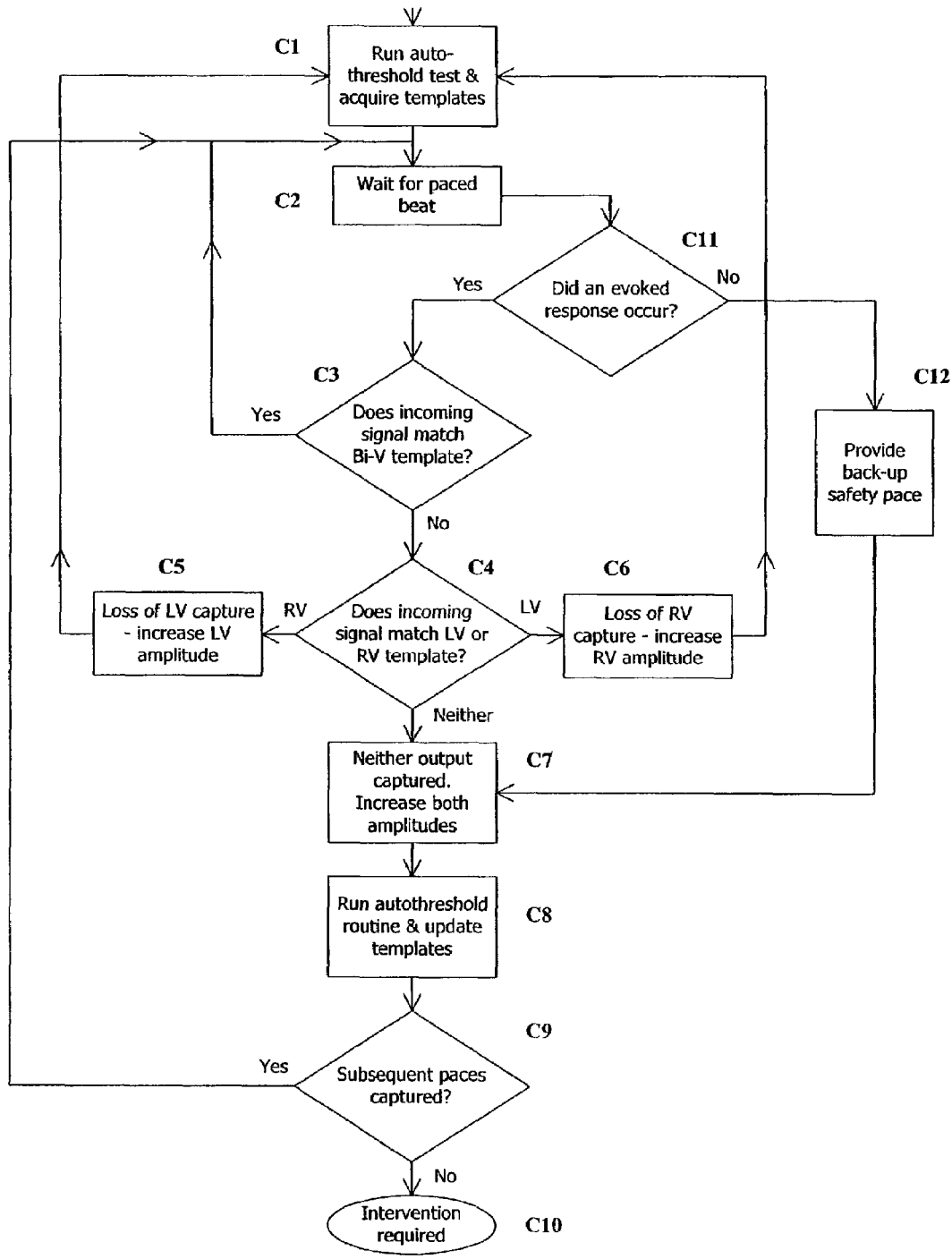

The auto-threshold algorithms illustrated in FIGS. 3A and 3B may be performed by either the pacemaker controller or the processor of an external programmer when it is desired to determine the capture thresholds for the RV and LV pacing channels and set the pacing amplitudes accordingly. As noted above, however, capture verification by cross-correlating template and test waveforms may also be performed on a beat-to-beat basis by the pacemaker controller to provide an ambulatory auto-capture function. FIGS. 4A and 4B illustrate exemplary algorithms for implementing auto-capture in which a capture verification test is performed with each pace.

Referring first to FIG. 4A, the controller performs an auto-threshold algorithm at step C1 in which templates are acquired in the RV-only, LV-only, and Bi-V pacing configurations and capture thresholds are determined for the LV and RV pacing channels so that the pacing pulse amplitudes can be set accordingly. The device then operates normally while the algorithm waits for a paced beat at step C2. At step C3, an incoming signal is used as a test waveform and cross-correlated with the Bi-V template to ascertain if both the RV and LV pacing pulses have achieved capture. If the Bi-V template and test waveforms are highly correlated, capture is assumed, and the algorithm loops back to step C2. If a lack of correlation between the test waveform and the Bi-V template is found, the algorithm separately cross-correlates the test waveform with the LV and RV templates at step C4. If the test waveform matches the RV template, lack of capture in the LV pacing channel is assumed. The LV pacing pulse amplitude is then increased at step C5, and the algorithm returns to step C1 so that updated templates can be acquired and an updated capture threshold determined. Similarly, if the test waveform matches the LV template, the RV pacing pulse amplitude is increased at step C6, and the algorithm returns to step C1. If neither the RV nor the LV paces have achieved capture as indicated by a lack of correlation between the test waveform and the two templates, both the RV and LV pacing amplitudes are increased at step C7. An auto-threshold algorithm is then performed at step C8, with the templates and capture thresholds updated and the pacing pulse amplitudes set accordingly. A capture verification test is performed at step C9 as the device operates with the updated pacing pulse amplitudes. If capture is achieved, the algorithm returns to the capture verification loop of steps C2 and C3. If subsequent paces still fail to achieve capture, it can be assumed that the lack of capture is due to factors other than pacing pulse energy such as the occurrence of fusion events (i.e., a capture by a pacing pulse coincident with an intrinsic contraction), difficulties in obtaining reference templates, or the occurrence of a malfunction in the pacemaker or lead system. An indication that further intervention is required is then logged in memory at step C10 which can be communicated to a clinician during the next communications session with an external programmer.

The ambulatory auto-capture algorithm presented in FIG. 4A relies on the inherent safety of having multiple ventricular pacing sites in the ventricle. In the event that one chamber loses capture, there is a low probability that the other chamber will simultaneously lose capture. Nonetheless, there is a possibility that the pacemaker could lose capture on both chambers simultaneously. When capture of the ventricles does not occur, it is desirable to provide a back-up safety pace to the right ventricle to immediately provide pacing therapy to prevent the patient from feeling light headed or loosing consciousness. Depending upon the particular implementation, the template cross-correlation algorithms presented here could take greater than 100 ms to accurately identify pacing activity. This is usually too long of a delay to deliver a safety pace. Further, if a fusion event occurs, the device must prevent pacing into a t-wave, so it must again react quickly if a safety pace is to be delivered. FIG. 4B is a flowchart diagram showing an ambulatory auto-capture algorithm that uses a traditional evoked response comparator in addition to template recognition. Steps C1 through C10 in FIG. 4B are identical to those described above with reference to FIG. 4A. After each paced beat, however, the algorithm also tests for capture at step C11 with an evoked response comparator that looks for any evoked response above a specified threshold following a pace. If any evoked response occurs from the ventricles, then some cardiac ventricular activity is assumed to have occurred, and the algorithm proceeds to step C3 to perform the template correlations and determine which chamber or chambers were captured. If no evoked response occurs following a pace, on the other hand, then the algorithm applies a safety pace to the right ventricle at step C12 and then proceeds as if neither pacing pulse captured by going to step C7. In this manner, the patient receives pacing therapy without a noticeable delay.

In the capture verification methods described above, a test depolarization waveform, such as an electrogram or ECG signal, is recorded and compared with one or more template waveforms. In certain implementations, this may involve the processor of the pacemaker or external programmer storing samples of a segment of the test waveform in memory and then performing the cross-correlation operation with corresponding samples of a template waveform. Recording and correlation of the test waveform with a template, however, may also be implemented by passing samples of the incoming electrogram or ECG signal through a finite impulse filter that performs the cross-correlation operation. In that case, the filter may be a matched filter having an impulse response equal to a time-reversed version of a template waveform. The test waveform is thus cross-correlated with a template waveform represented by the filter coefficients of the matched filter. Such a matched filter may be provided for each of the RV-only, LV-only, and BiV template waveforms and may be implemented either in code executed by the controller or as one or more dedicated hardware components.

Capture verification by comparing a test or evoked response depolarization waveform with a template has been described above in the context of multi-site pacing where either one or both of the paired atria or one or both of the paired ventricles are paced with multiple paces during a cardiac cycle. It should also be appreciated that a test depolarization waveform, such as an electrogram from an evoked response sensing channel, can be recorded during delivery of a single pacing pulse and then compared with a template waveform representing single-site capture of the heart by a pacing pulse in order to determine if capture has been achieved by the delivered pacing pulse.

c. Template Acquisition

Reliable determination of whether a pacing pulse has achieved capture by comparison of a test depolarization waveform with a reference template as described above requires that the reference template accurately reflect the particular evoked response being looked for. Simply recording a depolarization waveform during a pacing cycle with pulse energies known to be sufficient to achieve capture, however, does not guarantee a satisfactory reference template because of the possibility of PVC's, fusion events, or external noise. A PVC or premature ventricular contraction occurs when an intrinsic ventricular contraction occurs independently from excitation originating from the SA node. A fusion event is the occurrence of an intrinsic contraction coincident with capture of the heart by a pacing pulse. External noise may be produced by any source of electromagnetic energy such as a telemetry transmission from an external programmer. If any of these events occur while a reference template is being recorded, the resulting template will be a corrupted waveform that will not correlate with the desired capture event and will lead to erroneous results during an autothreshold routine. In order to avoid these problems and construct accurate templates, a template acquisition algorithm may be employed that takes advantage of the anomalous nature of the corrupting events.

Figure 5:
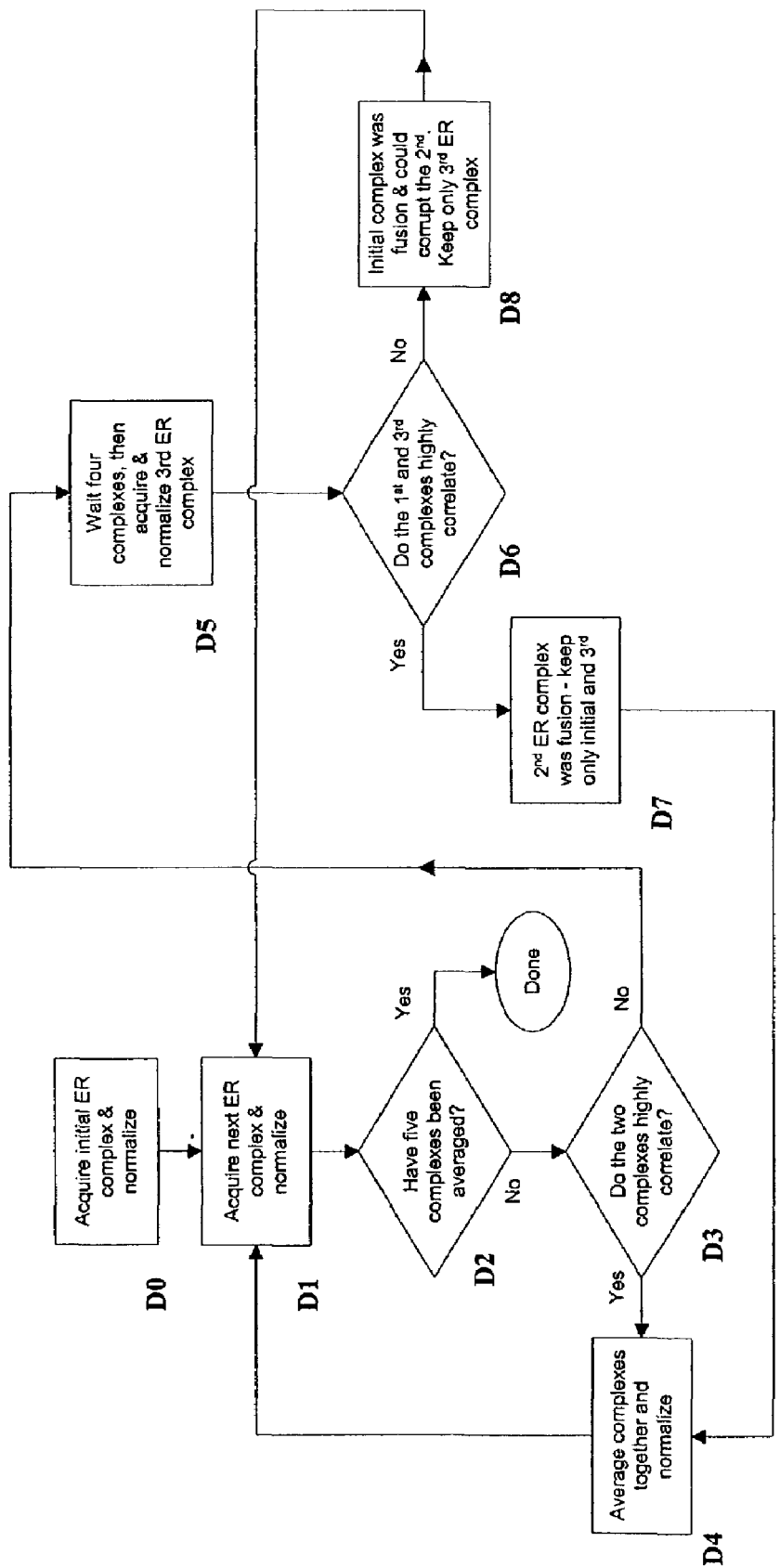
FIG. 5 illustrates an exemplary template acquisition algorithm.

FIG. 5 shows a flowchart of an exemplary template acquisition routine. In order to avoid recording fusion as well as other anomalous events as reference templates, the routine calculates the correlation coefficient (CC) of successive evoked responses and decides which responses to keep as templates based upon the CC. Initially, two evoked responses are collected and normalized at steps D0 and D1. The correlation between the two normalized evoked responses is calculated. If the two waveforms are found to highly correlate at step D3, then they are averaged together and the average is again normalized at step D4. The algorithm then returns to step D1 to acquire another evoked response. This process continues until five evoked responses are averaged together as tested for at step D2. If, on the other hand, the two complexes do not highly correlate at step D3, then the algorithm waits for several beats and then collects a third evoked response at step D5. Clinical data has indicated that PVCs or telemetry programming can affect the morphology of an evoked response for several beats. Waiting several beats thus allows any possible perturbation of the evoked response to complete before continuing. If the first and third evoked responses highly correlate at step D6, the second evoked response is regarded as noise or fusion. The second evoked response is then thrown out at step D7, and the first and third evoked responses are averaged at step D4. If the first and the third evoke responses do not highly correlate at step D6, then the initial complex is assumed to have been fusion. Because of the turbulence that can last several beats following a PVC or fusion, the first fusion event could have affected the second evoked response. Therefore, the algorithm keeps only the third evoked response at step D8 and begins again at step D1.

d. Discriminating Between Biventricular and Right-ventricular Capture

Figure 6:
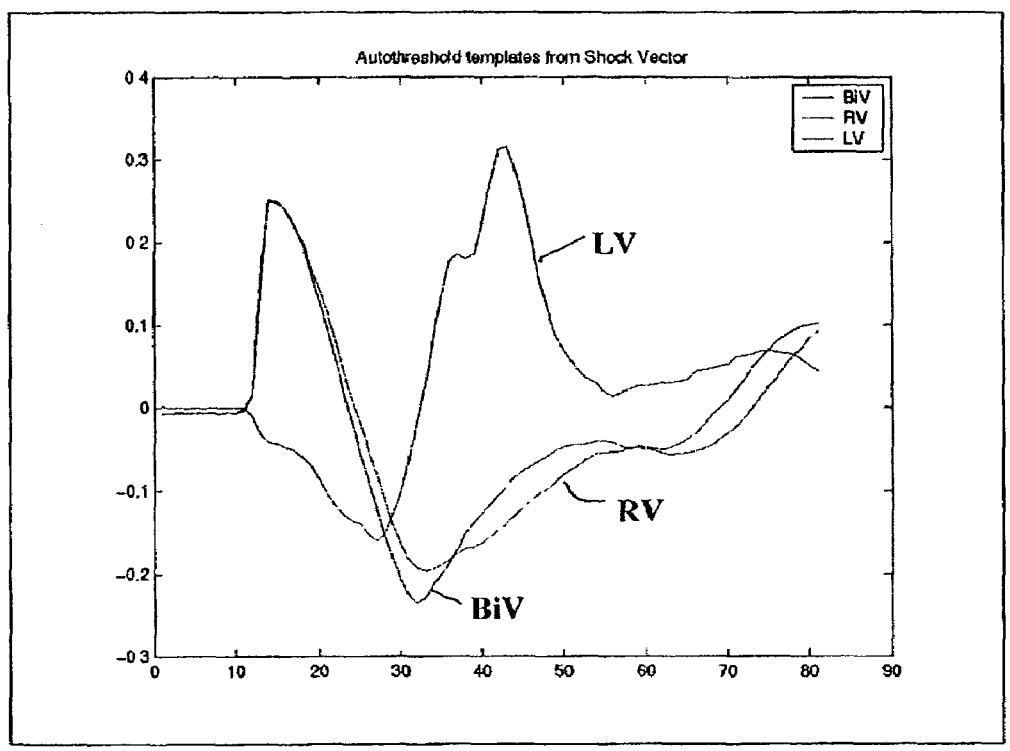
FIG. 6 shows examples of BiV, RV, and LV paced evoked responses.

FIG. 6 shows an example of BiV, RV, and LV paced evoked responses, each 400 ms in length, taken from one subject with the shock channel used as the evoked response sensing channel. As can be seen, the LV and BiV pacing cases produce great differences in the evoked responses. Considering that the shock electrodes are located in the right side of the heart, the sensing vector will be sensitive to a lack of activity from the right ventricle. This, of course, would also be true for any evoked response sensing channel with sensing electrodes on the right side of the heart. Conversely, the BiV and RV evoked responses display a high degree of similarity, correlating more than 95% in this particular subject. This is to be expected since both the RV and BiV paces will similarly contract the right ventricle tissue early in the r-wave complex. Much of the right ventricular cells are placed in refractory from the RV or BiV pace, allowing little further activity once the wavefront arrives from the left ventricular pace. Additionally, the magnitude of the signals from the right ventricle can swamp any far-field signals from the left side.

The high similarity of the BiV and RV templates in this example suggest that standard cross correlation techniques may not be sufficient for distinguishing between BiV and RV capture when the shock channel, or any sensing channel with electrodes located on the right side of the heart, is used as the evoked response sensing channel. A secondary criterion may therefore be used to fully discriminate between BiV and RV evoked responses with a right-sided sensing vector. It has been found that the highest level of difference between two such evoked responses occurs approximately 200 ms following a pace during the s-t transition. The normalized evoked responses to BiV and RV capture with a right-sided sensing vector in a number of experimental subjects have been found to be consistent and different during this time interval. This morphology difference can be used to distinguish between the BiV and RV capture by calculating the total energy in the normalized evoked response during a sub-window interval of 200–300 ms following the pace. The acquired BiV and RV templates are first used to calculate the energy in both templates. An energy bound can then be established by taking half of the energy difference:

$$E_{limit} = \frac{E_{max} - E_{min}}{2} + E_{min}$$

where $E_{max}$ is the larger of template energies, $E_{min}$ is the lesser value, and $E_{limit}$ is the energy bound or limit value. For example, the RV template may have a greater energy in the sub-window than the BiV template. A normalized evoked response with energy above the limit would then be classified as an RV capture, while a normalized evoked response with less total energy than the limit would be denoted as a BiV capture. Conversely, if the RV template has a lesser energy in the sub-window than the BiV template, an evoked response with greater total energy than the limit would be classified as a BiV capture. It should be appreciated that the same method could be used for discriminating between BiV and LV capture in the case where the evoked response sensing channel has sensing leads located on the left side of the heart.

In the method for BiV/RV capture discrimination just described, where the BiV and RV evoked response waveforms are similar due to right-sided sensing, BiV and RV capture are distinguished by measuring the total signal energy in a particular sub-window interval following the pace. Whether or not this BiV/RV capture discrimination method is needed depends upon both the particular patient and the electrode arrangement used for sensing the evoked response. Discussed below is a template-based capture verification algorithm that, among other things, employs the BiV/RV capture discrimination method and uses additional correlation criteria to determine when the method should be used.

e. Algorithm for Enhanced Discrimination of Evoked Responses

In the capture verification algorithms discussed above with respect FIGS. 3A–B and 4A–B, capture of one or both ventricles was assumed when the evoked response waveform was sufficiently correlated with a particular template waveform. Ideally, however, a template-based capture verification algorithm would reliably distinguish between one of five events: BiV capture, RV capture, LV capture, fusion, or asystole. Also, as discussed above, simple correlation of an evoked response with template waveforms representing left-ventricular, right-ventricular, or bi-ventricular capture may not be able to reliably distinguish between biventricular capture and capture of the ventricle where the evoked response sensing electrodes are located.

Figure 7:
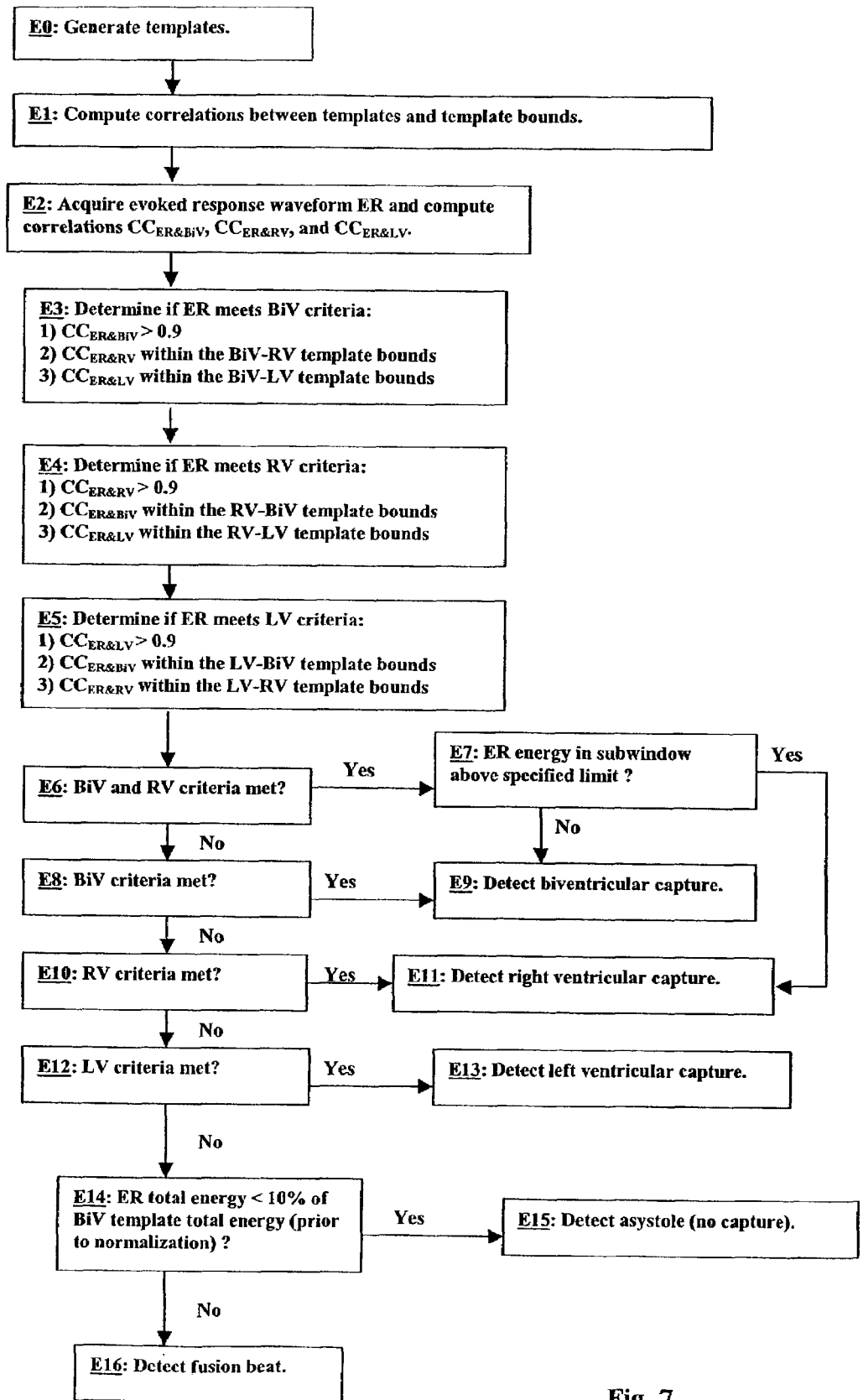
FIG. 7 illustrates an algorithm for enhanced discrimination between evoked responses.

A template-based capture verification algorithm which employs additional detection criteria to distinguish between all of the possible evoked response events is illustrated in FIG. 7. In order to add specificity to the algorithm, the evoked response waveform is correlated with template waveforms representing BiV, RV, and LV capture and is then classified according to whether it meets multiple criteria for BiV, RV, or LV capture. The multiple criteria for detecting each form of capture require not only a high degree of correlation with the template waveform representing that form of capture but also correlation values with the other template waveforms within specified ranges selected in accordance with the correlation between the different template waveforms. For example, an evoked response waveform will only be classified as meeting the criteria for BiV capture when it is highly correlated with the BiV template and correlated with the RV and LV templates to roughly the same extent as the BiV template. When an evoked response waveform meets the criteria for both BiV and RV capture, the method for BiV/RV discrimination using the signal energy in the subwindow interval discussed above is employed. If none of the capture criteria are met by the evoked response waveform, the algorithm then detects either asystole (i.e., no capture) or a fusion beat in accordance with the total signal energy in the evoked response waveform.

Referring to FIG. 7, the algorithm begins at step E0 with acquisition of templates. In order to ensure sufficient signal for a valid comparison, both the evoked response and template waveforms are recorded for 400 milliseconds following a pace. At an example sample rate of 200 Hz, an array of 80 samples constitutes each 400 ms recorded template or evoked response waveform. The algorithm generates the templates for BiV, RV, and LV capture events by pacing the heart in the appropriate pacing modes and recording the resulting waveforms. During template acquisition, the device is programmed with high pacing output voltages to ensure capture from the pacing outputs. The algorithm may also use the template acquisition routine described above with reference to FIG. 5 in order to ensure that the templates faithfully reflect the different capture events.

Figure 8:
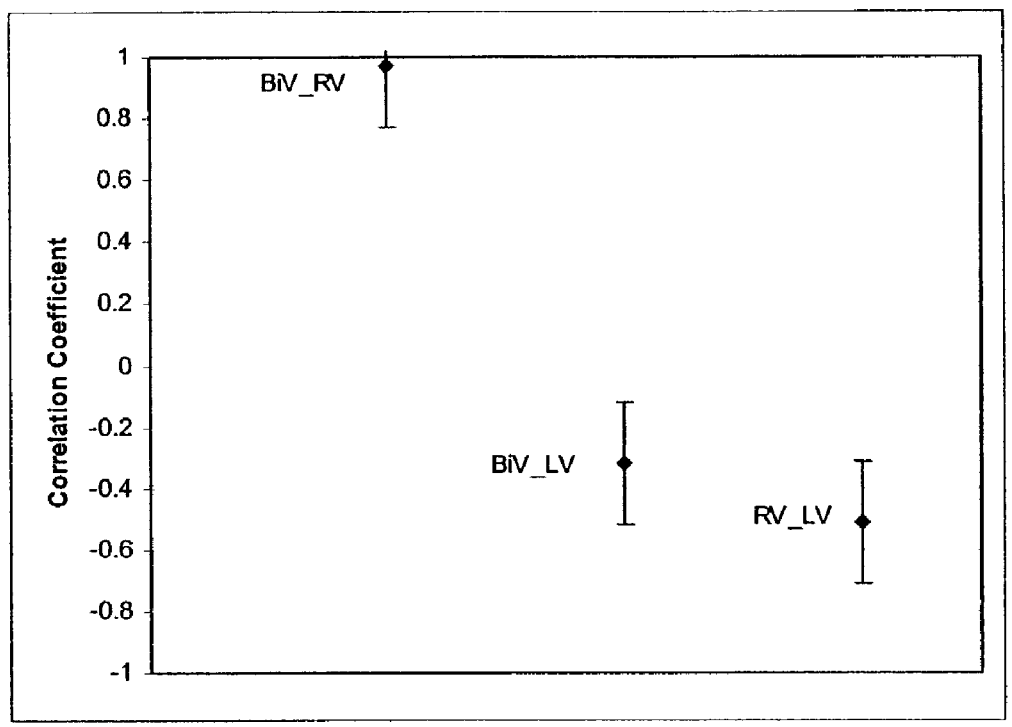
FIG. 8 shows a plot of the template correlation coefficients waveforms such as shown in FIG. 6.

Following the generation of the templates at step E0, the correlation coefficients between the templates are calculated at step E1 to measure the degree of similarity between all three templates. The correlation coefficients are calculated as follows:

$$CC = \frac{\sum_{i=1}^{n} x_i \cdot y_i}{\left[\sum_{i=1}^{n} x_i^2\right]^{1/2} \left[\sum_{i=1}^{n} y_i^2\right]^{1/2}}$$

where x is the first template, y is the second template, and n is the number of samples in the template. Note that the denominator terms are normalization factors for each template. Thus, three template correlation coefficients are produced: $CC_{BiV\&RV}$, $CC_{BiV\&LV}$, and $CC_{LV\&RV}$. These correlation coefficients between the templates are used to establish bounds to help classify evoked response waveforms. FIG. 8 shows a plot of the template correlation coefficients of the waveforms shown in FIG. 6. As might be expected, the similarity of the BiV and RV waveforms produces a high correlation between the two templates. Alternatively, the lack of similarity between the LV and both the RV and BiV waveforms yields a low correlation. Bounds are established at an exemplary +/−20 percentage points on either side of the calculated correlation coefficients. These bounds for the template cross-correlations can be used to more specifically detect particular capture events by determining if an evoked response not only highly correlates with one template but also correlates with the other two templates to an expected extent.

Once the templates and bounds have been properly established, the algorithm is ready to determine capture of subsequent paced beats at step E2. Following a pace, a 400 ms portion of the evoked response signal is collected and normalized:

$$ER_{norm} = \frac{ER}{\left[\sum_{i=1}^{n} (ER_i)^2\right]^{1/2}}$$

where ER is the evoked response waveform, and n is the number of samples in the waveform. Next, the ER waveform is cross-correlated with the templates by calculating a correlation coefficient between the normalized evoked response waveform and each normalized template:

$$CC_{ER\&BiV} = \sum_{i=1}^{n} ER_{norm,i} \cdot BiV_{norm,i}$$

$$CC_{ER\&RV} = \sum_{i=1}^{n} ER_{norm,i} \cdot RV_{norm,i}$$

$$CC_{ER\&LV} = \sum_{i=1}^{n} ER_{norm,i} \cdot LV_{norm,i}$$

Next, at steps E3 through E5, the evoked response is classified according to multiple criteria for each of the three possible capture events: BiV, RV, or LV capture. The evoked response may meet the criteria for one or more such events or may not meet any of the criteria. In order to meet the criteria for a particular capture event, the correlation coefficient of the evoked response waveform with the template for that capture event must be above a specified threshold (0.9 in this implementation), and the correlation coefficients of the evoked response waveform with the other must be within the bounds identified at step E1. As an example, assume the ER highly correlates with the BiV template, meeting the first criteria of step E3. If the cross correlations of the ER and the other two templates are within the bounds predicted by the earlier template analysis in step E2, the ER is classified as biventricular capture. In other words, if the ER closely matches the morphology of the BiV template and does not match the other templates in the expected manner, then the waveform is classified as biventricular capture.

After the ER waveform is classified according to the criteria of steps E3 through E5, subsequent steps determine the final detection result. If the ER waveform meets the criteria for both BiV and RV capture, as determined at step E6, then the total energy of the ER waveform in a sub-window 200–300 ms following the pace is utilized as a secondary discrimination criterion at step E7. If the total energy in the sub-window is above or below a specified limit, then RV capture is detected at step E11. Otherwise, BiV capture is detected at step E9. If the ER waveform is classified as meeting the criteria for only one capture event, the algorithm detects either BiV, RV, or LV capture at steps E8 through E13. If the ER waveform is classified as not meeting any other capture event criteria, the algorithm will detect either asystole or a fusion beat. If the total energy in the ER waveform is less than a specified threshold percentage (e.g., 10%) of the energy in the BiV template prior to normalization, as determined at step E14, then asystole is declared at step E15. Otherwise, since the ER waveform has been found to not meet any of the capture event criteria but is still representative of cardiac activity, the pace is classified as a fusion beat at step E16.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac pacemaker, comprising:
   first and second pacing channels, each such channel comprising an electrode for disposing near a chamber of the heart, a pulse generator for outputting pacing pulses, and a channel interface for adjusting the pacing pulse energy;
   a controller for controlling the operation of the pulse generators in accordance with a programmed pacing mode;
   an evoked response sensing channel comprising an electrode and a sense amplifier for sensing an evoked response generated after a pacing pulse; and,
   wherein the controller is programmed to:
   deliver first and second pacing pulses from the first and second pacing channels, respectively, to one or both of the paired atria or to one or both of the paired ventricles during a cardiac cycle;
   record an evoked response waveform from the evoked response sensing channel;

correlate the evoked response waveform with template waveforms representing capture by both pacing pulses, capture by the first pacing pulse, and capture by the second pacing pulse; and, classify the evoked response as representing a type of capture represented by a template waveform if the evoked response waveform highly correlates with one template waveform and has correlation values with the other template waveforms within specified bounds.

2. The pacemaker of claim 1 wherein the controller is programmed to classify the evoked response as representing a type of capture represented by a template waveform if the evoked response waveform highly correlates with one template waveform and correlates with the other template waveforms to roughly the same extent as the template waveform with which it highly correlates.

3. The pacemaker of claim 1 wherein the first and second pacing channels are right and left ventricular pacing channels, and the controller is programmed to classify the evoked response as representing right ventricular (RV) capture, left ventricular (LV) capture, or biventricular (BiV) capture by correlating the evoked response waveform with RV, LV, and BiV templates representing RV, LV, and BiV capture, respectively.

4. The pacemaker of claim 3 wherein the controller is programmed to:

classify the evoked response as representing BiV capture if the evoked response waveform highly correlates with the BiV template and correlates with each of the RV and LV templates to roughly the same extent as does the BiV template;

classify the evoked response as representing RV capture if the evoked response waveform highly correlates with the RV template and correlates with each of the BiV and LV templates to roughly the same extent as does the RV template; and, classify the evoked response as representing LV capture if the evoked response waveform highly correlates with the LV template and correlates with each of the RV and BiV templates to roughly the same extent as does the LV template.

5. The pacemaker of claim 4 wherein the controller is programmed to detect BiV, RV, or LV capture if the evoked response is classified as representing only one of either BiV, RV, or LV capture, respectively.

6. The pacemaker of claim 5 wherein the controller is programmed to detect BiV or RV capture in accordance with the signal energy of the evoked response within a specified sub-window time interval if the evoked response is initially classified as representing both RV and BiV capture.

7. The pacemaker of claim 6 wherein the controller is programmed to detect BiV or RV capture in accordance with whether the signal energy of the evoked response within the specified sub-window time interval is above or below a limit energy value between the signal energies of the BiV and RV templates in the event that the evoked response is initially classified as representing both RV and BiV capture.

8. The pacemaker of claim 6 wherein the specified sub-window time interval is approximately 200–300 ms following a pace.

9. The pacemaker of claim 3 wherein the controller is programmed to detect either asystole or a fusion beat in accordance with the total signal energy of the evoked response waveform in the event the evoked response waveform is not classified as either BiV, RV, or LV capture.

10. The pacemaker of claim 1 wherein the controller is programmed to acquire template waveforms representing capture by the first, second, or both pacing pulses by:

outputting a pacing pulse or pulses with sufficient energy to cause capture;

recording a first evoked response from a pacing pulse or pulses;

recording a second evoked response from a subsequent pacing pulse or pulses;

correlating the first and second recorded evoked responses; and, forming a template waveform by averaging the first and second recorded evoked responses only if the first and second template waveforms are correlated to a specified extent.

11. A method for operating a cardiac pacemaker, comprising:

outputting first and second pacing pulses to one or both of the paired atria or to one or both of the paired ventricles during a cardiac cycle in accordance with a programmed pacing mode;

sensing an evoked response generated after a pacing pulse;

recording an evoked response waveform from the evoked response sensing channel;

correlating the evoked response waveform with template waveforms representing capture by both pacing pulses, capture by the first pacing pulse, and capture by the second pacing pulse; and, classifying the evoked response as representing a type of capture represented by a template waveform if the evoked response waveform highly correlates with one template waveform and has correlation values with the other template waveforms within specified bounds.

12. The method of claim 11 further comprising classifying the evoked response as representing a type of capture represented by a template waveform if the evoked response waveform highly correlates with one template waveform and correlates with the other template waveforms to roughly the same extent as the template waveform with which it highly correlates.

13. The method of claim 11 wherein the first and second pacing pulses are output to the right and left ventricles, and further comprising classifying the evoked response as representing right ventricular (RV) capture, left ventricular (LV) capture, or biventricular (BiV) capture by correlating the evoked response waveform with RV, LV, and BiV templates representing RV, LV, and BiV capture, respectively.

14. The method of claim 13 further comprising:

classifying the evoked response as representing BiV capture if the evoked response waveform highly correlates with the BiV template and correlates with each of the RV and LV templates to roughly the same extent as does the BiV template;

classifying the evoked response as representing RV capture if the evoked response waveform highly correlates with the RV template and correlates with each of the BiV and LV templates to roughly the same extent as does the RV template; and, classifying the evoked response as representing LV capture if the evoked response waveform highly correlates with the LV template and correlates with each of the RV and BiV templates to roughly the same extent as does the LV template.

15. The method of claim 14 further comprising detecting BiV, RV, or LV capture if the evoked response is classified as representing only one of either BiV, RV, or LV capture, respectively.

16. The method of claim 15 further comprising detecting BiV or RV capture in accordance with the signal energy of the evoked response within a specified sub-window time interval if the evoked response is initially classified as representing both RV and BiV capture.

17. The method of claim 16 further comprising detecting BiV or RV capture in accordance with whether the signal energy of the evoked response within the specified sub-window time interval is above or below a limit energy value between the signal energies of the BiV and RV templates in the event is the evoked response is initially classified as representing both RV and BiV capture.

18. The method of claim 16 wherein the specified sub-window time interval is approximately 200–300 ms following a pace.

19. The method of claim 13 further comprising detecting either asystole or a fusion beat in accordance with the total signal energy of the evoked response waveform in the event the evoked response waveform is not classified as either BiV, RV, or LV capture.

20. The method of claim 19 further comprising detecting asystole if the total signal energy of the evoked response waveform is below a specified threshold.

* * * * *

UNITED STATES PATENT AND TRADEMARK OFFICE
CERTIFICATE OF CORRECTION

PATENT NO. : 7,286,876 B2 Page 1 of 1
APPLICATION NO. : 10/251629
DATED : October 23, 2007
INVENTOR(S) : Yonce et al.

It is certified that error appears in the above-identified patent and that said Letters Patent is hereby corrected as shown below:

In column 17, line 15, in Claim 17, after "event" delete "is" and insert -- that --, therefor.

Signed and Sealed this

Fifteenth Day of April, 2008

JON W. DUDAS
*Director of the United States Patent and Trademark Office*